US00PP37159P2

(12) United States Plant Patent
Smith

(10) Patent No.: US PP37,159 P2
(45) Date of Patent: Dec. 16, 2025

(54) ***CHRYSANTHEMUM* PLANT NAMED 'CIFZ0117'**

(50) Latin Name: ***Chrysanthemum* x *morifolium***
Varietal Denomination: CIFZ0117

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,474

(22) Filed: Feb. 4, 2025

(51) Int. Cl.
*A01H 5/02* (2018.01)
*A01H 6/14* (2018.01)

(52) U.S. Cl.
USPC ..... Plt./295

(58) Field of Classification Search
USPC ..... Plt./286, 287, 289, 295
See application file for complete search history.

*Primary Examiner* — Shubo Zhou
*Assistant Examiner* — Zachariah Allan Kay
(74) *Attorney, Agent, or Firm* — Dalea Skalla

(57) ABSTRACT

A new garden type *Chrysanthemum* plant named 'CIFZ0117' particularly distinguished by its medium to large size plant with round plant habit, a medium to large size decorative flower with yellow flower color, and a natural season response in mid to late September.

1 Drawing Sheet

Figure 1:
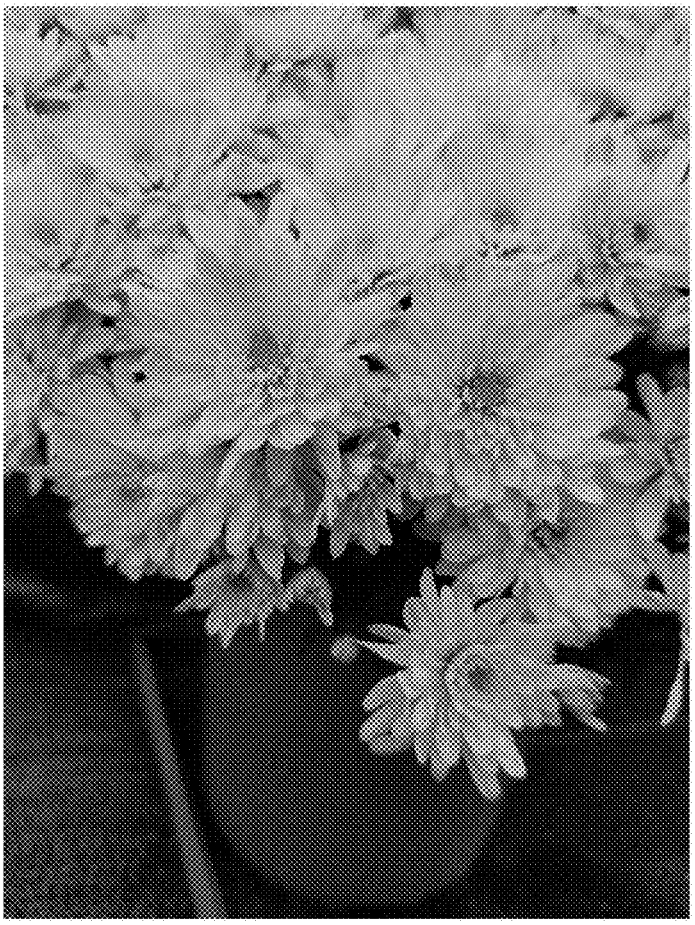

Latin name of the genus and species of the plant claimed: *Chrysanthemum x morifolium.*

Varietal denomination: 'CIFZ0117'.

BACKGROUND OF THE NEW PLANT

The present invention comprises a new *Chrysanthemum*, botanically known as *Chrysanthemum* x *morifolium*, and hereinafter referred to by the variety name 'CIFZ0117'.

'CIFZ0117' is a product of a planned breeding program. The new cultivar has medium to large size plant with round plant habit, a medium to large size yellow decorative flower, and a natural season response in mid to late September.

'CIFZ0117' originated from a cross made in fall of 2020 in Enkhuizen, The Netherlands. Seeds were sown in June 2021 in Alva, Florida and 'CIFZ0117' was selected from the resulting population on Nov. 4, 2021 in Alva, Florida.

The female parent was 'CIFZ0037', U.S. Plant Pat. No. 29,107.

TABLE 1

Characteristics of the female parent, compared to 'CIFZ0117':

| | 'CIFZ0117' | 'CIFZ0037', U.S. Plant Pat. No. 29,107 |
|---|---|---|
| Natural response: | 3 to 4 weeks slower | 3 to 4 weeks faster |
| Blackcloth response: | 0.5 week slower | 0.5 week faster |
| Flower size: | Similar or bit larger | Similar or bit smaller |
| Flower color: | Yellow | White |
| Plant habit: | Rounder | More upright |
| Flowering uniformity: | More uniform | Less uniform |

The male parent was an unnamed proprietary seedling 'FC0035', yellow daisy.

TABLE 2

Characteristics of the male parent, compared to 'CIFZ0117':

| | 'CIFZ0117' | 'FC0035' |
|---|---|---|
| Natural response: | 1 week slower | 1 week faster |
| Flower size: | Larger | Smaller |
| Flower type: | Decorative | Daisy |
| Plant size: | Larger | Smaller |
| Flower longevity: | Lasts longer | Shorter lived |
| Flowering uniformity: | More Uniform | Less Uniform |

The first act of asexual reproduction of 'CIFZ0117' was accomplished when vegetative cuttings were propagated from the initial selection in January 2022 in Alva, Florida.

BRIEF SUMMARY OF INVENTION

Horticultural examination of plants grown from cuttings of the plant initiated in January 2022 and continuing thereafter, has demonstrated that the combination of characteristics as herein disclosed for 'CIFZ0117' are firmly fixed and are retained through successive generations of asexual reproduction.

'CIFZ0117' has not been observed under all possible environmental conditions. The phenotype may vary significantly with variations in environment such as temperature, light intensity and day length.

A Plant Breeder's Right for this cultivar has not yet been applied for. 'CIFZ0117' has not been made publicly available prior to the effective filing date of this application, notwithstanding any disclosure that may have been made less than one year prior to the effective filing date of this application by the inventor or another who obtained 'CIFZ0117' directly from the inventor.

The following traits have been repeatedly observed and are determined to be basic characteristics of the new variety.

The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0117' with colors being as true as possible with an illustration of this type.

Figure 2:
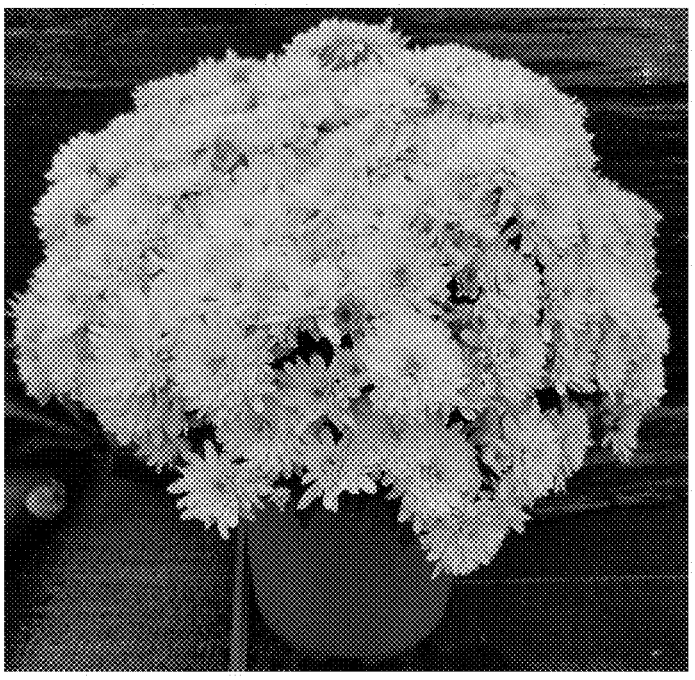

The photographic drawing shows in FIG. 1 a close view of flower of the new variety and in FIG. 2 a flowering plant from an indoor trial.

The aforementioned photographs: FIG. 1, as well as FIG. 2, were taken on Sep. 2, 2024 both showing a plant from the same blackcloth outdoor trial in Andijk, The Netherlands.

These plants were about 13 weeks of age. One rooted cutting per pot had been planted in a 19 cm pot, not pinched in week 23, 2024 and black clothed from week 29. Plants started flowering the end of August 2024.

The measurements were taken in Andijk, The Netherlands in September 2024 on plants from the same outdoor blackcloth trial

DETAILED BOTANICAL DESCRIPTION

Color references are made to The Royal Horticultural Society Colour Chart (R.H.S.) 2001.

TABLE 3

DIFFERENCES BETWEEN THE NEW VARIETY 'CIFZ0117' AND TWO MOST SIMILAR VARIETIES:

| | 'CIFZ0117' | 'Yomary', U.S. Plant Pat. No. 18,993 |
|---|---|---|
| Plant habit: | Rounder | More upright |
| Flower longevity: | 10% longer lasting | 10% shorter life |
| Foliage: | Greener | Paler |
| Flowering uniformity: | More uniform | Less uniform |

TABLE 4

| | 'CIFZ0117' | 'Stellar Yellow', Unpatented |
|---|---|---|
| Blackcloth response: | 0.5 week faster | 0.5 week slower |
| Flower size: | Larger | Smaller |
| Plant size: | Larger | Smaller |
| Plant strength: | Sturdier | Weaker |
| Flower longevity: | 50% longer lasting | 50% shorter life |

Plant:

*Form, growth and habit.*—Herbaccous garden-type, stems upright and outwardly spreading, freely branching.

*Plant height* (*above soil*).—18 cm.

*Plant height* (*inflorescence included*).—23 cm.

*Plant width.*—34 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 136A.

*Immature leaf, color lower surface.*—RHS 137B.

*Mature leaf, color, upper surface.*—RHS 139A.

*Mature leaf, color lower surface.*—RHS 137A.

*Length.*—9.5 cm.

*Width.*—4.5 cm.

*Shape.*—Ovate, with distinct lobes.

*Base shape.*—Shortly Attenuate.

*Apex shape.*—Apiculate.

*Margin.*—3, occasionally 4 or 5 lobed.

*Number of margin indentations.*—25-32.

*Depth of margin indentations.*—2-10 mm.

*Leaf length terminal lobe relative to total leaf length.*—1:2.

*Leaf depth lower lateral sinus.*—2.5 cm.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138B.

*Petiole Length.*—0.5 cm.

*Petiole orientation.*—Moderately upwards.

*Diameter.*—0.2 cm.

*Texture.*—Bifid hairs.

*Presence of stipules.*—No.

Stem:

*Quantity of main branches per plant.*—7-8.

*Color of stem.*—RHS 146C.

*Length of stem.*—9-12 cm.

*Diameter.*—0.3-0.4 cm.

*Length of internodes.*—1.5-3.0 cm.

*Texture.*—Bifid hairs.

*Color of peduncle.*—RHS 146B.

*Length of peduncle.*—4.0-6.0 cm.

*Peduncle diameter.*—0.2 cm.

*Texture.*—Bifid hairs.

Inflorescence:

*Type.*—Compositae, solitary, decorative inflorescences borne terminally above foliage, ligulate ray florets arranged in whorls on a capitulum giving a double flower.

*Quantity of short days to flowering* (*response time*).—Approximately 6.5 weeks.

*Quantity of inflorescences per plant.*—About 310 with some small buds developing.

*Lastingness of individual blooms on the plant.*—About six weeks from first color.

*Fragrance.*—Slightly spicy.

Bud (when showing color):

*Color.*—RHS 7C.

*Length.*—0.8 cm.

*Width.*—0.7 cm.

*Shape.*—Oblate.

Immature inflorescence (at moment of opening):

*Diameter.*—3.0 cm.

*Color of ray florets, upper surface.*—RHS 7A.

*Color of ray florets, lower surface.*—RHS 8A.

Mature inflorescence:

*Diameter.*—4.0 cm.

*Depth.*—1.6 cm.

*Total diameter of disc.*—0.6 cm.

*Receptacle color.*—RHS 138A.

*Receptacle height.*—0.3 cm.
*Receptacle diameter.*—1.2 cm.
*Length of corolla tube.*—0 cm.

Ray florets:
*Average quantity of florets.*—195.
*Number of whorls per inflorescence.*—12-13.
*Color of florets, upper surface.*—RHS 7A.
*Color lower surface.*—RHS 8A.
*Length.*—1.8 cm.
*Width/diameter.*—0.4 cm.
*Shape.*—Linear.
*Apex shape.*—Dentate.
*Base shape.*—Strongly concave.
*Margin.*—Entire. Small incisions may be present at tip.
*Margin.*—Type of rolling: moderately revolute.
*Texture, upper surface.*—Papillate.
*Lower surface.*—Papillate.
*Ribs present.*—Yes.
*Number of keels.*—2.
*Profile at widest point.*—Moderately convex.
*Longitudinal axis shape.*—Straight to weakly incurving.
*Corolla tube shape.*—No tube.

Disc florets:
*Number of disc florets.*—25-40.
*Width.*—0.1 cm.
*Length.*—0.3 cm.
*Colour.*—Base RHS 157C, top RHS 8A.
*Profile at widest point.*—Moderately convex.
*Longitudinal axis shape.*—Straight to weakly incurving.

Inflorescence (at moment of senescence):
*Color of ray florets, upper surface.*—RHS 7A.
*Color of ray florets, lower surface.*—RHS 8A.

Phyllaries:
*Quantity.*—24.
*Color, upper surface.*—RHS 138A.
*Color, lower surface.*—RHS 137A.
*Length.*—0.5 cm.
*Width.*—0.2 cm.
*Shape.*—Ensiform.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 1D.
*Style length.*—0.3 cm.
*Stigma color.*—RHS 8B.
*Stigma shape.*—Bi-parted.
*Ovary color.*—RHS 155D.
*Ovary length.*—0.2 cm.
*Ovary width.*—0.1 cm.

Androecium:
*Stamens.*—1, found on only disc florets.
*Color of filaments.*—RHS 157C.
*Length filaments.*—0.2 cm.
*Anther color.*—RHS 8B.
*Anther length.*—0.2 cm.
*Anther shape.*—Oval to club shaped.
*Color of pollen.*—RHS 13A.

What is claimed is:

1. A new and distinct variety of *Chrysanthemum* plant named 'CIFZ0117' substantially as illustrated and described herein.

* * * * *